United States Patent [19]

Gal

[11] 4,230,893

[45] Oct. 28, 1980

[54] 1,1-DI(4-HYDROXY-3-METHOXYPHENYL)-2-ALKOXYPROPANE

[75] Inventor: George Gal, Watchung, N.J.

[73] Assignee: Merck & Co., Inc., Rahway, N.J.

[21] Appl. No.: 75,345

[22] Filed: Sep. 13, 1979

[51] Int. Cl.³ ............... C07C 43/20; C07C 101/77
[52] U.S. Cl. ................... 568/640; 562/446; 568/322
[58] Field of Search .................... 568/640

[56] References Cited

U.S. PATENT DOCUMENTS

| | | | |
|---|---|---|---|
| 2,744,882 | 5/1956 | Bender et al. | 568/640 |
| 2,868,818 | 1/1959 | Pfister et al. | 562/446 |
| 2,967,892 | 1/1961 | Smith | 568/640 |
| 3,210,428 | 10/1965 | Guest et al. | 568/640 |

FOREIGN PATENT DOCUMENTS 1444897 8/1976 United Kingdom.

OTHER PUBLICATIONS

Pearl et al., J. Org. Chem., 16, 221, (1951).

Primary Examiner—G. T. Breitenstein
Attorney, Agent, or Firm—Daniel T. Szura; Theresa Y. Cheng

[57] ABSTRACT

4-Hydroxy-3-methoxyphenylacetone, an intermediate for methyldopa, has been prepared from reacting two moles of guaiacol and one mole of a 2-alkoxy propanol followed by basic elimination to form the enol ether of 4-hydroxy-3-methoxy phenyl acetone. The enol ether is subsequently converted to 4-hydroxy-3-methoxy phenyl acetone upon treatment with a strong acid.

3 Claims, No Drawings

1,1-DI(4-HYDROXY-3-METHOXYPHENYL)-2-ALKOXYPROPANE

BACKGROUND

This invention relates to a process for preparing 4-hydroxy-3-methoxyphenylacetone which is an intermediate for the important antihypertensive agent, methyldopa.

The use of 4-hydroxy-3-methoxyphenylacetone in the methyldopa synthesis has been disclosed in U.S. Pat. No. 2,868,818 which comprises (1) the addition of a cyanide anion to 4-hydroxy-3-methoxyphenylacetone to form 4-methyl-4-(4-hydroxy-3-methoxybenzyl)-hydantoin; (2) basic hydrolysis of the hydantoin to afford α-methyl-β-(4-hydroxy-3-methoxyphenyl)alanine; and (3) subsequent hydrolysis with hydrobromic acid to form methyldopa, i.e., α-methyl-β-(3,4-dihydroxyphenyl)alanine.

Presently, 4-hydroxy-3-methoxyphenylacetone is manufactured from vanillin and nitroethane (Pearl et al, J. Org. Chem., 16, p. 221, 1951). The process suffers from the high cost of vanillin and a sole supplier for nitroethane.

For these reasons, an alternate synthesis of 4-hydroxy-3-methoxyphenylacetone is desirable to safeguard the continuous production of methyldopa.

The novel process of this invention comprises three steps:

(1) formation of a 1,1-di(4-hydroxy-3-methoxyphenyl)-2-alkoxypropane (I) (diguaiacyl-2-alkoxypropane) from reacting two moles of 1-hydroxy-2-methoxybenzene (guaiacol) and one mole of 2-alkoxypropanal; and (2) basic elimination of compound (I) to form the enol ether of 4-hydroxy-3-methoxyphenylacetone; and (3) conversion to the parent phenylacetone upon treatment with strong acid.

The acid catalyzed condensation between guaiacol and unsubstituted propanal is known (German Pat. No. 2,418,973). According to the German patent, the resulting 1,1-diguaiacylpropane undergoes thermal cleavage to afford 1-guaiacylpropene in the presence of a basic catalyst. However, the German patent does not suggest the present invention because it is well known in the art that α-oxy-substituted aldehydes such as α-acetoxy or α-methoxypropanal behave differently from unsubstituted propanal such as used in the German patent. As shown below, an α-oxy-substituted aldehyde has a great tendency to eliminate the oxy function under acidic conditions.

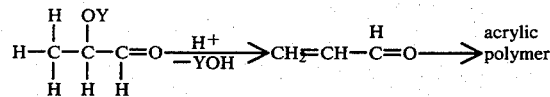

Furthermore, the notorious ability of the resulting acrylaldehyde to polymerize would have led to the expectation that the guaiacol-propanal condensation would not be extrapolated to α-oxysubstituted aldehydes due to the latter's superseding decomposition rate. This expectation has actually been realized by the failure of α-acetoxypropanal to react with guaiacol at all. Instead, acetic acid is eliminated and the resulting acrylaldehyde polymerizes as expected.

Therefore, it is totally unexpected that α-alkoxypropanal would condense with guaiacol under acid catalysis to yield the desired diguaiacyl-2-alkoxypropane.

Accordingly, it is an object of the present invention to provide a new, alternate process for the production of 4-hydroxy-3-methoxyphenylacetone.

It is also an object of this invention to provide a process which is economically more advantageous than the current manufacturing process based on vanillin.

Still another object of the present invention is to provide the novel 1,1-diguaiacyl-2-alkoxypropanes as useful intermediates for 4-hydroxy-3-methoxyphenylacetone.

DETAILED DESCRIPTION OF THE INVENTION

The present invention concerns a process for preparing 4-hydroxy-3-methoxyphenylacetone according to the following scheme,

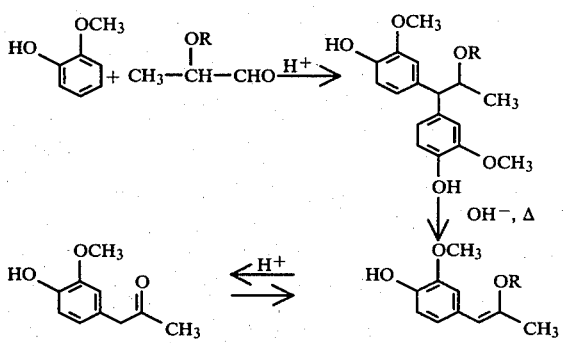

wherein R is loweralkyl especially $C_{1-5}$ alkyl such as methyl, ethyl, isopropyl, t-butyl, or isopentyl.

The acidic condensation between guaiacol and 2-alkoxypropanal is carried out in an acidic medium such as aqueous sulfuric acid, hydrochloric acid, p-toluenesulfonic acid, 2,4-dinitro-phenylsulfonic acid, formic acid, or a strong cation exchange resin on the hydrogen cycle such as IR-120 or Dowax 50 WX4, phosphoric acid, acetic acid, trichloroacetic acid, trifluoroacetic acid or a mixture thereof at a temperature ranging from about −5° C. to about 30° C. The concentration of guaiacol is about 2–6 g/g of the acidic medium. Preferably, the reaction is carried out in 50%–80% by weight aqueus sulfuric acid containing about 5%–25% by weight of acetic acid to homogenize the substrates at about 0° C.–15° C. Even more preferably, the condensation is carried out in 65%–72% by weight aqueous sulfuric acid containing about 15% by weight acetic acid at about 5° C.–10° C., with a concentration of guaiacol at about 3 g/g of the acidic medium. Normally, a 1–2 fold excess of guaiacol over 2-alkoxypropanal is maintained, and it takes about 2–16 hours for the reaction to reach substantial completion. Under the more preferred conditions, the reaction is substantially complete within about five hours. The resulting 1,1-diguaiacyl-2-alkoxypropane is cleaved at about 200° C.–270° C. at 6–12 mm. vacuo in the presence of about 0.5–5 mole percent strong base. Sodium hydroxide, potassium hydroxide or sodium alkoxide such as sodium methoxide, sodium butoxide or potassium ethoxide can be used although sodium hydroxide and potassium hydroxide are preferred. The simultaneously distilled cleavage product, 1-(4-hydroxy-3-methoxyphenyl)-2-alkoxy-1-propene, is treated with a strong acid such as sulfuric, hydrochloric, phosphoric acid or a mixture thereof in a refluxing inert aromatic solvent at about 70° C.–150° C. until a substantial conversion to 4-hydroxy-3-methoxyphenylacetone is accomplished. The refluxing usually requires about 0.5–6 hours and the inert aromatic solvent includes benzene, toluene or xylene, preferably toluene. In a preferred embodiment, the conversion is affected by refluxing the cleavage product in toluene containing 10%–20% aqueous sulfuric acid for about 1–2 hours.

As a stable intermediate for 4-hydroxy-3-methoxyphenylacetone which in turn is a useful intermediate for methyldopa, the novel 1,1-diguaiacyl-2-alkoxypropanes are also embodiments of this invention.

The following example illustrates the present invention.

EXAMPLE 1

4-Hydroxy-3-methoxyphenylacetone

Step (a): Preparation of 1,1-di(4-hydroxy-3-methoxyphenyl)-2-ethoxypropane

To a mixture of guaiacol (150 g., 1.21 M), acetic acid (6 g.) and 65% aqueous sulfuric acid (36 g.) is added 2-ethoxypropanal (30.6 g.) over a period of 60 minutes. The mixture is stirred at 0° C.–5° C. under nitrogen for five hours. Cold water is added and the entire mixture is extracted with methylene chloride. The methylene chloride layer is separated, dried over magnesium sulfate, and concentrated in vacuo to afford 178.9 g. of crude product. Purification of the crude product via fractional distillation at 194° C.–195° C. at 0.2 mm. vacuo gives 66.8 g. of pure 1,1-di(4-hydroxy-3-methoxyphenyl)-2-ethoxypropane.

Step (b): Preparation of 1-(4-hydroxy-3-methoxyphenyl)-2-ethoxy-1-propene 1,1-Diguaiacyl-2-ethoxypropane (16.3 g.) is heated after the addition of 40 mg. KOH in a distillation apparatus with a 3 cm. Vigreux column attachment. A mixture of guaiacol and 1-(4-hydroxy-3-methoxyphenyl)-2-ethoxy-1-propene is distilled off at a bath temperature of 250° C.–260° C. and at 10 mm vacuo. A total of 6.8 g. product is obtained. 1-(4-Hydroxy-3-methoxyphenyl)-2-ethoxy-1-propene can be isolated in pure form by fractional distillation, b.p.: 111° C.–116° C. at 0.5 mm. vacuo.

Step (c): Preparation of 4-Hydroxy-3-methoxyphenylacetone

A two-phase mixture of 1.93 g. 1-(4-hydroxy-3-methoxyphenyl)-2-ethoxy-1-propene in 10 ml. 14% sulfuric acid and 10 ml. of toluene is refluxed in nitrogen atmosphere for one hour. After cooling it to ambient temperature the organic phase is separated, dried over sodium sulfate and concentrated in vacuo, yielding 1.71 g. (95% pure by gc) of 4-hydroxy-3-methoxyphenylacetone.

Employing substantially the same procedure of Example 1, Step (a), but substituting for 2-ethoxypropanal used therein 2-methoxy- or 2-(n-butoxy)propanal, there are prepared the corresponding 1,1-di-(4-hydroxy-3-methoxyphenyl)-2-methoxypropane and 1,1-di-(4-hydroxy-3-methoxyphenyl)-2-(n-butoxy)propane. The 1,1-di-(4-hydroxy-3-methoxyphenyl)-2-alkoxypropanes obtained above are subsequently converted to 4-hydroxy-3-methoxyphenylacetone via step (b) and step (c) of Example 1.

What is claimed is:

1. A compound of structural formula:

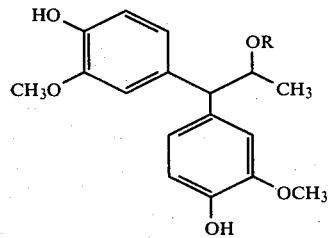

wherein R is $C_{1-5}$ alkyl.

2. The compound of claim 1 wherein R is methyl or ethyl.

3. 1,1-Di(4-hydroxy-3-methoxyphenyl)-2-ethoxypropane.

* * * * *